(12) United States Patent
Hillebrand et al.

(10) Patent No.: US 6,677,268 B2
(45) Date of Patent: Jan. 13, 2004

(54) CATALYST BASED ON COBALT AND/OR RHODIUM EMPLOYED IN A TWO-PHASE MEDIUM

(75) Inventors: Gerhard Hillebrand, Rueil Malmaison (FR); Andre Hirschauer, Montesson (FR); Dominique Commereuc, Meudon (FR); Helene Olivier-Bourbigou, Rueil Malmaison (FR); Lucien Saussine, Croissy sur seine (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 10/193,705

(22) Filed: Jul. 12, 2002

(65) Prior Publication Data

US 2003/0055299 A1 Mar. 20, 2003

Related U.S. Application Data

(63) Continuation-in-part of application No. 09/730,795, filed on Dec. 7, 2000, now Pat. No. 6,469,216.

(30) Foreign Application Priority Data

Dec. 8, 1999 (FR) .............................. 99/15.573

(51) Int. Cl.$^7$ .................... B01J 31/00; C07F 15/05; C07C 45/50; C09K 3/00
(52) U.S. Cl. .................... 502/155; 502/166; 252/182.3; 546/2; 546/10; 548/101; 548/108; 548/402; 556/137; 556/138; 556/141; 568/451; 568/454; 568/455
(58) Field of Search ................... 568/451, 454, 568/455; 556/137, 138, 141; 546/2, 10; 548/101, 108, 402; 502/155, 166; 252/182.3

(56) References Cited

U.S. PATENT DOCUMENTS

| | | | | | |
|---|---|---|---|---|---|
| 3,565,823 A | * | 2/1971 | Parshall | ...................... | 502/164 |
| 3,832,391 A | * | 8/1974 | Parshall | ...................... | 560/233 |
| 4,390,729 A | * | 6/1983 | Oswald | ...................... | 568/454 |
| 4,608,444 A | * | 8/1986 | Jacobson | ...................... | 568/462 |
| 4,725,568 A | * | 2/1988 | Parker et al. | ................ | 502/159 |
| 5,874,638 A | | 2/1999 | Chauvin et al. | ............. | 568/454 |

FOREIGN PATENT DOCUMENTS

| | | |
|---|---|---|
| EP | 0107430 | 5/1984 |
| EP | 0776880 | 6/1997 |
| EP | 0924182 | 6/1999 |

OTHER PUBLICATIONS

Applied Homogeneous Catalysis with Organometallic Compounds, A Comprehensive Handbook in Three Volumes, vol. 1: Applications, edited by Boy Cornils and Wolfgang A. Herrmann, Second, Completely Revised and Enlarged Edition, Wiley–VCH, pp. 186–188.

* cited by examiner

*Primary Examiner*—Porfirio Nazario-Gonzalez
(74) *Attorney, Agent, or Firm*—Millen, White, Zelano & Branigan, P.C.

(57) ABSTRACT

An improved catalyst based on cobalt and/or rhodium dissolved in a non-aqueous ionic solvent which is liquid at a temperature of less than 90° C. More particularly, the catalyst comprises at least one complex of cobalt and/or rhodium co-ordinated with at least one nitrogen-containing ligand and the non-aqueous ionic solvent comprises at least one quaternary ammonium and/or phosphonium cation and at least one inorganic anion.

18 Claims, No Drawings

CATALYST BASED ON COBALT AND/OR RHODIUM EMPLOYED IN A TWO-PHASE MEDIUM

CROSS REFERENCE TO RELATED APPLICATION

This is a continuation-in-part of application Ser. No. 09/730,795 filed Dec. 7, 2000 now U.S. Pat. No. 6,469,216 B2.

The present invention relates to an improved catalyst based on cobalt and/or rhodium used in a two-phase medium. The catalyst based on cobalt and/or rhodium, which comprises at least one cobalt and/or rhodium complex co-ordinated with at least one nitrogen-containing ligand, is dissolved in a non-aqueous ionic solvent which is liquid at a temperature of less than 90° C., in which the aldehydes formed are slightly soluble or insoluble. The catalyst is particularly useful for the hydroformylation of olefinically unsaturated compounds.

Hydroformylation of olefinic compounds is a reaction of major industrial importance and the majority of processes use homogeneous catalysts dissolved in an organic phase constituted by the reactants, products and possibly excess ligand, although difficulties are encountered in separating and recovering the catalyst, in particular when it is used in relatively large quantities, as is the case with catalysts based on cobalt or on a noble metal, as is the case with rhodium-based catalysts.

DESCRIPTION OF RELATED ART

One solution aimed at solving that problem has been developed by Bartik et al., Organometallics (1993), 12, 164–170, J. Organometal. Chem. (1994), 480, 15–21, and by Beller et al., J. molecular Catal. A: Chemical (1999), 143, 31–39. It consists of carrying out hydroformylation in the presence of an aqueous solution containing a cobalt complex which is rendered water-soluble by the presence of a phosphine-sulfonate ligand such as the sodium salt of trisulfonated triphenylphosphine or a trisulfonated tris-(alkylphenyl)phosphine. International Patent Application WO 97/00132 describes cobalt clusters substituted by tri-alkoxysilylmethyl groups which render them water-soluble. In that manner, the organic phase containing the aldehydes is readily separated from the aqueous phase containing the catalyst.

A further solution aimed at solving that problem has been described in French Patent No. 2 314 910. It consists of carrying out hydroformylation in the presence of an aqueous solution containing a rhodium complex which is rendered water-soluble by the presence of a sulfonated phosphine ligand which is itself water-soluble, such as the sodium salt of trisulfonated triphenylphosphine. In that manner, the organic phase containing the aldehydes is readily separated from the aqueous phase containing the catalyst. That technique has been studied widely and those studies have been discussed in an article by W. A. Herrmann in "Angewandte Chemie International", 1993, volume 32, pages 1524 ff.

Despite the huge industrial importance of such techniques for hydroformylation of propylene, such two-phase systems suffer from a lack of solubility of olefins in water, leading to relatively low reaction rates, which render them unsuitable for long chain olefins.

U.S. Pat. No. 3,565,823 describes a technique consisting of dispersing a transition metal compound in a quaternary ammonium or phosphonium salt of tin or germanium with formula $(R^1R^2R^3R^4Z)YX_3$ where $R^1$, $R^2$, $R^3$, and $R^4$ are hydrocarbyl residues containing up to 18 carbon atoms, Z is nitrogen or phosphorous, Y is tin or germanium and X is a halogen, for example chlorine or bromine.

U.S. Pat. No. 3,832,391 claims a process for olefin carbonylation using the same composition. The above compositions have the disadvantage of having a relatively high melting point, for example over 90° C., which complicates manipulation of the catalyst solutions and the reaction products.

U.S. Pat. No. 5,874,638 describes that it is possible to benefit both from the advantages of a two-phase operation while avoiding the disadvantages linked to using water and to using compounds with a high melting point, by dissolving certain catalytic compounds of transition metals from groups 8, 9 and 10, known to catalyze hydroformylation, in non-aqueous ionic solvents which are constituted by organic-inorganic salts which are liquid at ambient temperature.

SUMMARY OF THE INVENTION

It has now been discovered that the activity and selectivity for the hydroformylation reaction of catalysts based on cobalt and/or rhodium used in an ionic non-aqueous solvent which is liquid at a temperature of less than 90° C. are greatly improved by using nitrogen-containing ligand to complex the cobalt and/or rhodium. The present invention focuses on the novel catalyst system.

More precisely, the invention provides a catalyst composition comprising at least one complex of cobalt and/or rhodium co-ordinated by at least one nitrogen-containing ligand, and of at least one non-aqueous ionic solvent comprising at least one organic-inorganic salt with general formula $Q^+A^-$, where $Q^+$ represents a quaternary ammonium and/or quaternary phosphonium cation and $A^-$ represents an anion, with the provision that the at least one ligand is devoid of tertiary phosphines, stibnines, arsines and phosphates.

The cobalt and/or rhodium precursor compounds of the catalyst are selected from the group formed by cobalt and/or rhodium salts such as acetylacetonates, carboxylates, in particular formate or acetate, and carbonyl complexes, such as dicobalt-octacarbonyl, cobalt-tetracarbonyl hydride, rhodium-dicarbonyl acetylacetonate and carbonyl clusters. The choice of the cobalt and/or rhodium precursor compound is not critical, but in general it is preferable to avoid halides.

The nitrogen-containing ligand is preferably selected from the group formed by monoamines, di-, tri- and polyamines, imines, diimines, pyridine and substituted pyridines, bipyridine, imidazole and substituted imidazoles, pyrrole and substituted pyrroles, pyrazole and substituted pyrazoles. Non limiting examples which can be cited are triethylamine, ethylene diamine, tetramethyl-ethylenediamine, diethylenetriamine, diazabicyclooctane, 1,4,7-trimethyl-1,4,7-triazacyclononane, N,N'-dimethyl-ethane-1,2-diimine, N,N'-di-tert-butyl-ethane-1,2-diimine, N,N'-di-t-butyl-butane-2,3-diimine, N,N'-diphenyl-ethane-1,2-diimine, N,N'-bis-(2,6-dimethylphenyl)-ethane-1,2-diimine, N,N'-bis-(2,6-diisopropyl-phenyl)-ethane-1,2-diimine, N,N'-bis-(2,6-di-t-butyl-phenyl)-ethane-1,2-diimine, N,N'-diphenyl-butane-2,3-diimine, N,N'-bis-(2,6-dimethyl-phenyl)-butane-2,3-diimine, N,N'-bis-(2,6-diisopropyl-phenyl)-butane-2,3-diimine, N,N'-bis-(di-t-butyl-2,6-phenyl)-butane-2,3-diimine, pyridine, picolines, t-butylpyridine, bipyridine, di-t-butyl-bipyridine, imidazole, N-methylimidazole, N-butylimidazole, benzimidazole, pyrrole, N-methylpyrrole and 2,6-dimethylpyrrole.

The nitrogen-containing ligand can also include other organic functions, such as alcohol, aldehyde, ketone, carboxylic acid, ester, nitrile, quaternary ammonium and/or phosphonium, also sulfonium functions. Non limiting examples which can be cited are picolinic acids and esters, 2,6-dialkoxypyridines, salicylaldimines, 2,6-bis-N-aryliminopyridines, 1-dialkyl (and diaryl) phosphino-2-(4-pyridyl)ethanes, alkyl 2-(4-pyridyl)-acetates, alkyl 2-(2-pyridyl)-acetates, ethylene glycol bis-3-(4-pyridyl)-propanoate, 2-(2-pyridyl)-ethanol, 3-(2-pyridyl)-propanol and 3-(2-pyridyl)-propyl acetate.

The non-aqueous ionic solvent is selected from the group formed by liquid salts with general formula $Q^+A^-$ where $Q^+$ represents quaternary ammonium and/or quaternary phosphonium and $A^-$ represents any anion which can form a liquid salt at low temperature, i.e., below 90° C. and advantageously at most 85° C., preferably below 50° C. Preferred anions $A^-$ are acetate, halogenoacetate, tetrafluoroborate, tetrachloroborate, hexafluorophosphate, hexafluoroantimonate, fluorosulfonate, perfluoroalkylsulfonate, bis-(perfluoroalkylsulfonyl)amide and arene-sulfonate ions.

The quaternary ammonium and/or phosphonium ions preferably have general formula $NR^1R^2R^3R^{4+}$ and $PR^1R^2R^3R^{4+}$ or general formula $R^1R^2N=CR^3R^{4+}$ or $R^1R^2P=CR^3R^{4+}$, where $R^1$, $R^2$, $R^3$, and $R^4$, which may be identical or different, represent hydrogen (with the exception of the $NH_4^+$ cation for $NR^1R^2R^3R^{4+}$), preferably a single substituent representing hydrogen, or hydrocarbyl residues containing 1 to 12 carbon atoms, for example saturated or unsaturated alkyl, cycloalkyl or aromatic generals, aryl or aralkyl groups containing 1 to 12 carbon atoms. The ammonium and/or phosphonium can also be a derivative of nitrogen-containing and/or phosphorus-containing heterocycles containing 1, 2 or 3 nitrogen and/or phosphorus atoms, in which the cycles are constituted by 4 to 10 atoms, preferably 5 to 6 atoms.

The quaternary ammonium and/or phosphonium can also be a cation with formula:

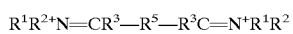

and/or

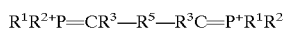

where $R^1$, $R^2$ and $R^3$, which may be identical or different, are defined as above, and $R^5$ represents an alkylene or phenylene residue. Examples of groups $R^1$, $R^2$, $R^3$, and $R^4$ which can be mentioned include the following radicals: methyl, ethyl, propyl, isopropyl, butyl, secondary butyl, tertiary butyl, amyl, methylene, ethylidiene, phenyl or benzyl; $R^5$ can be a methylene, ethylene, propylene or phenylene group. The ammonium and/or phosphonium cation is preferably selected from the group formed by N-butylpyridinium, N-ethylpyridinium, 3-ethyl-1-methylimidazolium, 3-butyl-1-methylimidazolium, diethylpyrazolium, pyridinium, trimethylphenyl ammonium and tetrabutyl-phosphonium. Examples of salts which can be used in the invention which can be cited are N-butylpyridnium hexafluorophosphate, N-ethylpyridinium tetrafluoroborate, tetrabutylphosphonium tetrafluoroborate, 3-butyl-1-methylimidazolium tetrafluoroborate, 3-butyl-1-methylimidazolium hexafluoroantimonate, 3-butyl-1-methylimidazolium hexafluorophosphate, 3-butyl-1-methylimidazolium trifluoromethylsulfonate, pyridinium fluorosulfonate and trimethylphenylammonium hexafluorophosphate. These salts can be used alone or as a mixture.

The catalytic composition is obtained by mixing the liquid salt with the cobalt and/or rhodium compound and the nitrogen-containing ligand in any known manner. It is also possible to first dissolve the transition metal compound (cobalt and/or rhodium) and/or the ligand in the organic solvent.

The complex between the cobalt and/or rhodium precursor and the nitrogen-containing ligand can be prepared prior to the reaction by mixing the cobalt and/or rhodium precursor with the ligand in a suitable solvent, for example an organic solvent or the non-aqueous ionic solvent which will then by used in the catalytic reaction. The complex can also be prepared in situ by mixing the cobalt and/or rhodium precursor and the nitrogen-containing ligand directly in the hydroformylation reactor.

In general, the catalytic composition can contain a miscible or partially miscible organic solvent such as an aromatic hydrocarbon, and/or a non-miscible aliphatic hydrocarbon which enables better phase separation. Preferably, the catalytic composition contains no water.

The concentration of cobalt and/or rhodium complex in the ionic liquid "molten salt" is not critical. It is advantageously in the range 0.1 moles per liter of "molten salt" to 5 moles per liter, preferably in the range 1 mole to 1 mole per liter, still more preferably in the range 100 to 500 moles per liter. The mole ratio between the nitrogen-containing ligand and the cobalt and/or rhodium compound is in the range 0.1 to 100, preferably in the range 1 to 20.

The components in the composition of the invention can be mixed in any order at a temperature in the range −20° C. to 200° C., preferably in the range 0° C. to 140° C., and advantageously in the range 20° C. to 90° C.

Olefinically unsaturated compounds which can be hydroformylated are selected from the group formed by monoolefins, diolefins, in particular conjugated diolefins and olefinic compounds comprising one or more heteroatoms, in particular unsaturated compounds such as compounds with a ketone function or a carboxylic acid function. Examples which can be cited are hydroformylation of pentenes to hexanal and methylpentanal, hexenes to isoheptanals, isooctenes to isononanals. These olefinic compounds can be used pure or diluted with saturated or unsaturated hydrocarbons.

The ratio of the partial pressures of hydrogen to carbon monoxide used in the reaction medium for hydroformylation can be 10:1 to 1:10, preferably in a ratio of 1:1, but any other ratio can be used depending on the implementation of the process.

The temperature at which hydroformylation is carried out is in the range 30° C. to 200° C.; advantageously the temperature is less than 150° C., preferably in the range 50° C. to less than 150° C. The pressure can be in the range 1 MPa to 20 MPa, preferably in the range 2 MPa to 15 MPa.

Catalytic hydroformylation of the unsaturated compounds can be carried out in a closed system, in a semi-open system or continuously with one or more reaction stages. At the reactor outlet, the organic phase containing the reaction products is advantageously separated by simple decantation of the ionic solvent phase containing the "molten salt" and the major portion of the catalyst. This ionic solvent phase, which contains at least a portion of the catalyst, is at least partially returned to the reactor, the other portion optionally being treated to eliminate the catalyst residues.

The entire disclosure of all applications, patents and publications, cited above and below, and of corresponding French application 99/15573, filed Dec. 8, 1999, are hereby incorporated by reference.

The following examples illustrate examples of using the catalyst of the invention without limiting its scope.

EXAMPLE 1

A hydroformylation reaction was carried out in a 300 ml volume stainless steel reactor provided with a double envelope to regulate the temperature by circulating a heat exchange fluid, and provided with an efficient stirring means with counteracting blades. 0.4 g of dicobalt-octacarbonyl (i.e., 2.3 millimoles of cobalt), 0.16 g of pyridine (2 millimoles), 10 ml of butyl-methyl-imidazolium tetrafluoroborate, 30 ml of heptane and 30 ml of hexene-1 were introduced into this autoclave, which had first been purged of air and moisture and placed under a mixture of hydrogen and carbon monoxide (1/1 molar) at atmospheric pressure. The pressure of the hydrogen-carbon monoxide mixture (1/1 molar) was brought to 10 MPa, the temperature was increased to 125° C. and stirring was commenced. After 6 hours, stirring was stopped and the reaction mixture was allowed to cool and decant, then the pressure was released. After extraction from the autoclave, the upper organic phase was slightly colored. The hexene-1 conversion was 98.9% by weight. The selectivity for C7 aldehydes was 88.9% and the n/iso (n-heptanal/isoheptanals) ratio was 1.9.

EXAMPLE 2

A hydroformylation reaction was carried out in the same apparatus and using the same operating procedure as that described in Example 1. 0.4 g of dicobalt-octacarbonyl (i.e., 2.3 millimoles of cobalt), 0.16 g of pyridine (2 millimoles), 10 ml of butyl-methyl-imidazolium tetrafluoroborate, 30 ml of heptane and 30 ml of a C6 olefin cut containing 7.4% of 2,3-dimethyl-butene-1, 12.1% of 2,3-dimethyl-butene-2, 23.5% of 2-methyl-pentene-1 and 57% of 2-methyl-pentene-2 was introduced. The pressure of the hydrogen-carbon monoxide mixture (1/1 molar) was brought to 12 MPa, the temperature was increased to 90° C. and stirring was commenced. After 6 hours, stirring was stopped and the reaction mixture was allowed to cool and decant, then the pressure was released. After extraction from the autoclave, the upper organic phase was slightly colored. The C6 olefin conversion was 66% by weight. The selectivity for C7 aldehydes was 60%. The other products were hexanes (18%) and heavy products.

EXAMPLE 3

A hydroformylation reaction was carried out in the same apparatus and using the same operating procedure as that described in Example 1. 0.35 g of dicobalt-octacarbonyl (i.e., 2 millimoles of cobalt). 0.28 g of 1-dicyclopentyl-2-phosphino-(4-pyridyl)-ethane (1 millimole), 10 ml of butyl-methyl-imidazolium tetrafluoroborate, 10 ml of heptane and 30 ml of hexene-1 were introduced. The pressure of the hydrogen-carbon monoxide mixture (1/1 molar) was brought to 11 MPa, the temperature was increased to 140° C. and stirring was commenced. After 6 hours, stirring was stopped and the reaction mixture was allowed to cool and decant, then the pressure was released. After extraction from the autoclave, the upper organic phase was very slightly colored. The hexene-1 conversion was 83.8% by weight. The selectivity for C7 aldehydes was 52.8% and the n/iso (n-heptanal/isoheptanals) ratio was 1.6. The other products were hexene-2 and hexene-3 (11%) and heavy products.

EXAMPLE 4

A hydroformylation reaction was carried out in the same apparatus and using the same operating procedure as that described in Example 1. 1.6 g of dicobalt-octacarbonyl (i.e., 9.3 millimoles of cobalt), 3.3 g of ethylene glycol bis-3-(4-pyridyl)-propanoate (10 millimoles), 10 ml of butyl-methyl-imidazolium tetrafluoroborate, 30 ml of heptane and 30 ml of hexene-1 were introduced. The pressure of the hydrogen-carbon monoxide mixture (1/1 molar) was brought to 9.5 MPa, the temperature was increased to 95° C. and stirring was commenced. After 6 hours, stirring was stopped and the reaction mixture was allowed to cool and decant, then the pressure was released. After extraction from the autoclave, the upper organic phase was practically colorless. The hexene-1 conversion was 65% by weight. The selectivity for C7 aldehydes was 67% and the n/iso (n-heptanal/isoheptanals) ratio was 4.2. The other products were C7 alcohols (11%) and heavy products.

EXAMPLE 5

A hydroformylation reaction was carried out in the same apparatus and using the same operating procedure as that described in Example 1. 1.6 g of dicobalt-octacarbonyl (i.e., 9.3 millimoles of cobalt), 3.3 g of bis-3-(4-pyridyl)-propanoate ethylene glycol (2.4 millimoles), 10 ml of butyl-methyl-imidazolium tetrafluoroborate, 30 ml of heptane and 30 ml of hexene-1 were introduced. The pressure of the hydrogen-carbon monoxide mixture (1/1 molar) was brought to 8 MPa, the temperature was increased to 80° C. and stirring was commenced. After 6 hours, stirring was stopped and the reaction mixture was allowed to cool and decant, then the pressure was released. After extraction from the autoclave, the upper organic phase was slightly colored. The hexene-1 conversion was 68% by weight. The selectivity for C7 aldehydes was 90% and the n/iso (n-heptanal/isoheptanals) ratio was 3.9.

EXAMPLE 6

A hydroformylation reaction was carried out in the same apparatus and using the same operating procedure as that described in Example 1. 0.4 g of dicobalt-octacarbonyl (i.e., 2.3 millimoles of cobalt), 0.6 g of 3-(2-pyridyl)-propanol (4.4 millimoles), 0.75 ml of butyl-methyl-imidazolium tetrafluoroborate, 30 ml of heptane and 30 ml of hexene-1 were introduced. The pressure of the hydrogen-carbon monoxide mixture (1/1 molar) was brought to 6.5 MPa, the temperature was increased to 95° C. and stirring was commenced. After 6 hours, stirring was stopped and the reaction mixture was allowed to cool and decant, then the pressure was released. After extraction from the autoclave, the upper organic phase was slightly colored. The hexene-1 conversion was 58% by weight. The selectivity for C7 aldehydes was 92.8% and the n/iso (n-heptanal/isoheptanals) ratio was 3.9.

EXAMPLE 7

A hydroformylation reaction was carried out in the same apparatus and using the same operating procedure as that described in Example 1. 0.4 g of dicobalt-octacarbonyl (i.e., 2.3 millimoles of cobalt), 0.72 g of 3-(2-pyridyl)-propyl acetate (4 millimoles), 9 ml of butyl-methyl-imidazolium bis-(trifluoromethylsulfonyl) amide, 30 ml of heptane and 30 ml of hexene-1 were introduced. The pressure of the hydrogen-carbon monoxide mixture (1/1 molar) was brought to 9 MPa, the temperature was increased to 95° C. and stirring was commenced. After 6 hours, stirring was stopped and the reaction mixture was allowed to cool and decant, then the pressure was released. After extraction from the autoclave, the upper organic phase was slightly yellow in color. The hexene-1 conversion was 86% by weight. The selectivity for C7 aldehydes was 84.6% and the n/iso (n-heptanal/isoheptanals) ratio was 2.8.

EXAMPLE 8

A hydroformylation reaction was carried out in the same apparatus and using the same operating procedure as that described in Example 1. 0.4 g of dicobalt-octacarbonyl (i.e., 2.3 millimoles of cobalt), 0.8 g of N,N'-bis-(2,6-diisopropylphenyl)-butane-2,3-diimine (2 millimoles), 6 ml of butyl-methyl-imidazolium tetrafluoroborate, 30 ml of heptane and 30 ml of hexene-1 were introduced. The pressure of the hydrogen-carbon monoxide mixture (1/1 molar) was brought to 9.4 MPa, the temperature was increased to 90° C. and stirring was commenced. After 6 hours, stirring was stopped and the reaction mixture was allowed to cool and decant, then the pressure was released. After extraction from the autoclave, the upper organic phase was slightly colored. The hexene-1 conversion was 95.5% by weight. The selectivity for C7 aldehydes was 89.3% and the n/iso (n-heptanal/isoheptanals) ratio was 3.

EXAMPLE 9

A hydroformylation reaction was carried out in the same apparatus and using the same operating procedure as that described in Example 1. 0.4 g of dicobalt-octacarbonyl (i.e., 2.3 millimoles of cobalt), 0.72 g of 3-(2-pyridyl)-propyl acetate (4 millimoles), 6 ml of tetra(hexyloctyl)-phosphonium tetrafluoroborate, 30 ml of heptane and 30 ml of hexene-1 were introduced. The pressure of the hydrogen-carbon monoxide mixture (1/1 molar) was brought to 8.1 MPa, the temperature was increased to 95° C. and stirring was commenced. After 6 hours, stirring was stopped and the reaction mixture was allowed to cool and decant, then the pressure was released. After extraction from the autoclave, the upper organic phase was slightly colored. The hexene-1 conversion was 57% by weight. The selectivity for C7 aldehydes was 80% and the n/iso (n-heptanal/isoheptanals) ratio was 2.4.

EXAMPLE 10 (COMPARATIVE)

A hydroformylation reaction was carried out in the same apparatus and using the same operating procedure as that described in Example 1. 0.35 g of dicobalt-octacarbonyl (i.e., 2 millimoles of cobalt), 0.5 g of tri-n-butylphosphine (2.5 millimoles), 10 ml of butyl-methyl-imidazolium tetrafluoroborate, 10 ml of heptane and 30 ml of hexene-1 were introduced. The pressure of the hydrogen-carbon monoxide mixture (1/1 molar) was brought to 10 MPa, the temperature was increased to 125° C. and stirring was commenced. After 6 hours, stirring was stopped and the reaction mixture was allowed to cool and decant, then the pressure was released. After extraction from the autoclave, the upper organic phase was slightly colored. The hexene-1 conversion was 21% by weight. The selectivity for C7 aldehydes was 34% and the n/iso(n-heptanal/isoheptanals) ratio was 2.7. Comparison with Example 1 shows the beneficial effect of a nitrogen-containing ligand over the phosphorous-containing ligands of the prior art.

EXAMPLE 11

A hydroformylation reaction was carried out in the same apparatus and using the same operating procedure as that described in Example 1. 19.3 mg of rhodium-dicarbonyl acetylacetonate, 30.3 mg of N,N'-bis-(2,6-diisopropylphenyl)-butane-2,3-diimine, 5 g of tributyl-tetradecylphosphonium tetrafluoroborate, 2 ml of heptane and 7.5 ml of hexene-1 were introduced. The pressure of the hydrogen-carbon monoxide mixture (1/1 molar) was brought to 2 MPa, the temperature was increased to 80° C. and stirring was commenced. After 5 hours, stirring was stopped and the reaction mixture was allowed to cool and decant, then the pressure was released. After extraction from the autoclave, the upper organic phase was slightly colored. The hexene-1 conversion was 48% by weight. The selectivity for C7 aldehydes was 60% and the n/iso (n-heptanal/isoheptanals) ratio was 2.4.

EXAMPLE 12

A hydroformylation reaction was carried out in the same apparatus and using the same operating procedure as that described in Example 1. 19.3 mg of rhodium-dicarbonyl acetylacetonate, 18.3 mg of 2,2'-bipyridyl-4,4'-dicarboxylic acid, 4 ml of butyl-methyl-imidazolium tetrafluoroborate, 2 ml of heptane and 7.5 ml of hexene-1 were introduced. The pressure of the hydrogen-carbon monoxide mixture (1/1 molar) was brought to 2 MPa, the temperature was increased to 80° C. and stirring was commenced. After 5 hours, stirring was stopped and the reaction mixture was allowed to cool and decant, then the pressure was released. After extraction from the autoclave, the upper organic phase was slightly colored. The hexene-1 conversion was 75% by weight. The selectivity for C7 aldehydes was 66% and the n/iso (n-heptanal/isoheptanals) ratio was 1.2.

The preceding examples can be repeated with similar success by substituting the generically or specifically described reactants and/or operating conditions of this invention for those used in the preceding examples.

From the foregoing description, one skilled in the art can easily ascertain that the catalyst composition, though indicated to be especially useful for hydroformylation, can also be used for other reactions, for example, in butadiene carbonylation reactions of which the synthesis of adipic acid is especially important. For a further explanation of such reactions, reference is invited to "Applied Homogeneous Catalysis with Organometallic Compounds" edited by Boy Cornils and Wolfgang A. Herrmann, volume 1, pages 186–188, second edition, Wiley-VCH. For any given reaction, a chemist, using routine experimentation, would be capable of selecting optimum operating conditions when utilizing the catalyst of the present invention.

What is claimed is:

1. A composition comprising at least one complex of at least one of cobalt and rhodium co-ordinated by at least one nitrogen-containing ligand, and at least one non-aqueous ionic solvent comprising at least one organic-inorganic salt with general formula $Q^+A^-$, where $Q^+$ represents at least one quaternary radical selected from the group consisting of quaternary ammonium and quaternary phosphonium, and $A^-$ represents an anion, with the proviso that said complex is devoid of tertiary phosphines, stibines, arines and phosphates.

2. A composition according to claim 1, wherein said at least one complex of at least one of cobalt and rhodium is formed from a precursor selected from the group consisting of cobalt and rhodium salts and carbonyl complexes.

3. A composition according to claim 1, wherein said at least one complex is formed from an acetylacetonate, carboxylate, dicobalt-octacarbonyl, cobalt-tetracarbonyl hydride, rhodium-dicarbonyl acetyl-acetonate or carbonyl cluster.

4. A composition according to claim 1, wherein the nitrogen-containing ligand is selected from the group consisting of monoamines, di-, tri- and polyamines, imines, diimines, pyridine and substituted pyridines, bipyridine, imidazole and substituted imidazoles, pyrrole and substituted pyrroles and pyrazole and substituted pyrazoles.

5. A composition according to claim 4, wherein the nitrogen-containing ligand is pyridine or a substituted pyridine.

6. A composition according to claim 4, wherein the nitrogen-containing ligand is imidazole or a substituted imidazole.

7. A composition according to claim 4, wherein the nitrogen-containing ligand is an imine or a diimine.

8. A composition according to claim 1, wherein the non-aqueous ionic solvent is selected from the group consisting of liquid salts with general formula $Q^+A^-$ where $Q^+$ represents quaternary ammonium and/or quaternary phosphonium and $A^-$ represents any anion which can form a liquid salt at below 90° C.

9. A composition according to claim 8, wherein $A^-$ is an acetate, halogenoacetate, tetrafluoroborate, tetrachloroborate, hexafluorophosphate, hexafluoroantimonate, fluorosulfonate, perfluoroalkylsulfonate, bis-(perfluoroalkylsulfonyl)amide or arene-sulfonate ion.

10. A composition according to claim 8 wherein the quaternary radical is of the formula $NR^1R^2R^3R^{4+}$, $PR^1R^2R^3R^{4+}$, $R^1R^2N=CR^3R^{4+}$, or $R^1R^2P=CR^3R^{4+}$, where $R^1$, $R^2$, $R^3$, and $R^4$, which may be identical or different, represent hydrogen with the exception of the $NH_4^+$ cation for $NR^1R^2R^3R^{4+}$, or hydrocarbyl residues containing 1 to 12 carbon atoms.

11. A composition according to claim 8 is a derivative of at least one of nitrogen-containing and phosphorus-containing heterocycle containing 1, 2 or 3 nitrogen and/or phosphorus atoms, in which the cycles are constituted by 4 to 10 atoms.

12. A composition according to claim 8, wherein the quaternary radical is at least one cation selected from the group consisting of:

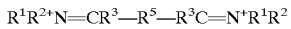

and

where R1, R2 and R3, which may be identical or different, are defined as in claim 10, and R5 represents an alkylene or phenylene residue.

13. A composition according to claim 8, wherein the quaternary radical is selected from the group consisting of N-butylpyridinium, N-ethylpyridinium, 3-ethyl-1-methylimidazolium, 3-butyl-1-methyl-imidazolium, diethylpyrazolium, pyridinium, trimethylphenyl ammonium and tetrabutyl-phosphonium.

14. A composition according to claim 8, wherein the non-aqueous ionic solvent is selected from the group consisting of N-butylpyridnium hexafluorophosphate, N-ethylpyridinium tetrafluoroborate, tetrabutylphosphonium tetra-fluoroborate, 3-butyl-1-methylimidazolium tetrafluoroborate, 3-butyl-1-methylimidazolium hexafluoroantimonate, 3-butyl-1-methylimidazolium hexafluorophosphate, 3-butyl-1-methyl-imidazolium trifluoromethylsulfonate, pyridinium fluorosulfonate and trimethylphenyl-ammonium hexafluorophosphate.

15. A composition according to claim 1, wherein the concentration of cobalt and/or rhodium complex in the liquid ionic solvent is in the range of 0.1 to 5 moles per liter, and the mole ratio between the nitrogen-containing ligand and the cobalt and/or rhodium part of the coordinated complex is in the range of 0.1 to 100.

16. A composition according to claim 10, wherein only one $R^1$, $R^2$, $R^3$ and $R^4$ represents hydrogen.

17. A composition according to claim 11, wherein the heterocycles contain 5 or 6 atoms.

18. A composition according to claim 1, wherein said ligand is a compound consisting of carbon, nitrogen, hydrogen and optionally at least one of oxygen and sulfur.

* * * * *